United States Patent [19]

Vicario

[11] Patent Number: 4,781,700

[45] Date of Patent: Nov. 1, 1988

[54] DEVICE FOR TAKING FROM A VEIN SAMPLES OF BLOOD TO BE TESTED

[75] Inventor: Guido F. Vicario, Milan, Italy

[73] Assignee: Finbiomedica S.R.L., Milan, Italy

[21] Appl. No.: 62,586

[22] Filed: Jun. 16, 1987

[30] Foreign Application Priority Data

Jun. 17, 1986 [IT] Italy .................. 20818 A/86

[51] Int. Cl.[4] .................. A61M 5/245; A61B 5/00
[52] U.S. Cl. .................. 604/234; 604/155; 604/201; 128/760; 128/765
[58] Field of Search .............. 128/760, 763, 764, 765; 604/154, 155, 187, 200, 201, 205, 232, 233, 234, 235

[56] References Cited

U.S. PATENT DOCUMENTS

| | | | |
|---|---|---|---|
| 2,691,372 | 10/1954 | Lores | 604/201 |
| 3,123,073 | 3/1964 | Barr, Sr. et al. | 128/764 |
| 3,456,649 | 7/1969 | Jewett | 604/155 |
| 3,480,014 | 11/1969 | Callahan | 604/201 |
| 3,528,404 | 9/1970 | Chan | 128/764 |
| 3,612,321 | 10/1971 | Roger | 604/189 |
| 3,765,402 | 10/1973 | Grabhorn . | |
| 3,776,218 | 12/1973 | Svensson | 128/765 |
| 3,835,835 | 9/1974 | Thompson et al. . | |
| 4,370,987 | 2/1983 | Bazell et al. | 128/765 |
| 4,378,812 | 4/1983 | Sarstedt | 128/765 |
| 4,459,997 | 7/1984 | Sarstedt | 128/765 |
| 4,563,175 | 1/1986 | LaFond . | |
| 4,639,248 | 1/1987 | Schweblin | 128/765 |

FOREIGN PATENT DOCUMENTS 0029126 5/1981 European Pat. Off. .
8204387 12/1982 Int'l Pat. Institute. ............ 128/764

Primary Examiner—Stephen C. Pellegrino
Assistant Examiner—Ralph Lewis
Attorney, Agent, or Firm—Young & Thompson

[57] ABSTRACT

The device for collecting blood specimens by venipuncture for laboratory tests consists of a hollow support fitted with a double-ended needle at one end and a vial with a plunger that can be fitted into and removed from the cavity in the support, the vial being sealed at one end by a pierceable membrane. In a preferred embodiment a mechanical system for automatic operation of the plunger is also envisaged. The double-ended needle consists of an active needle that enters the vein, positioned eccentrically to the axis of the support, and a passive needle that punctures the vial membrane eccentrically.

5 Claims, 2 Drawing Sheets

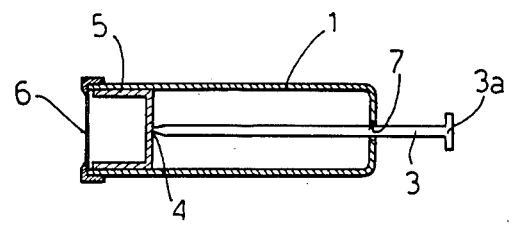
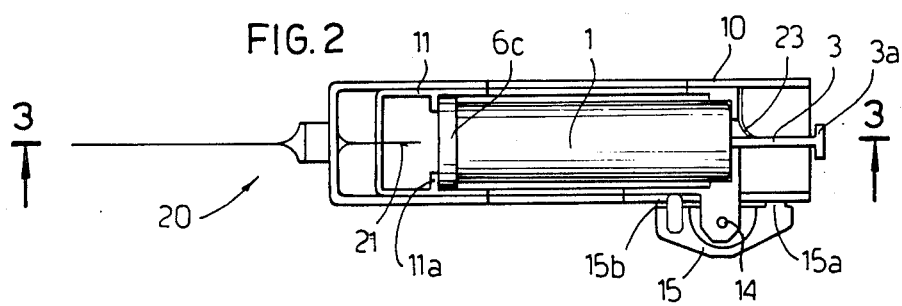
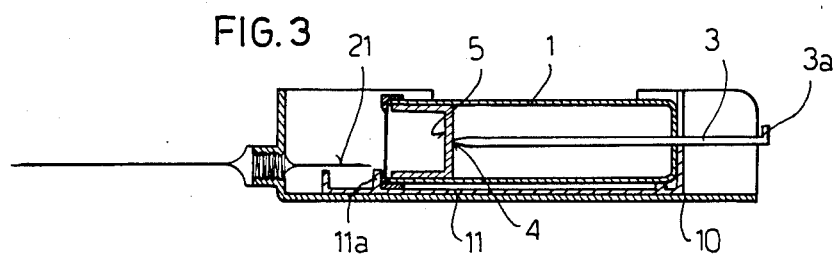
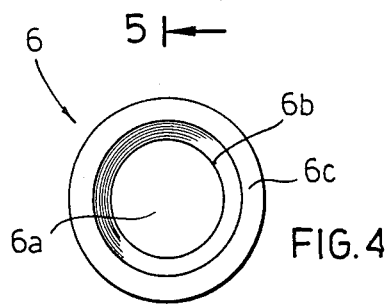
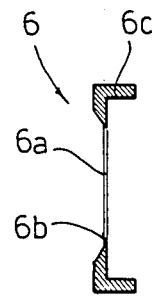

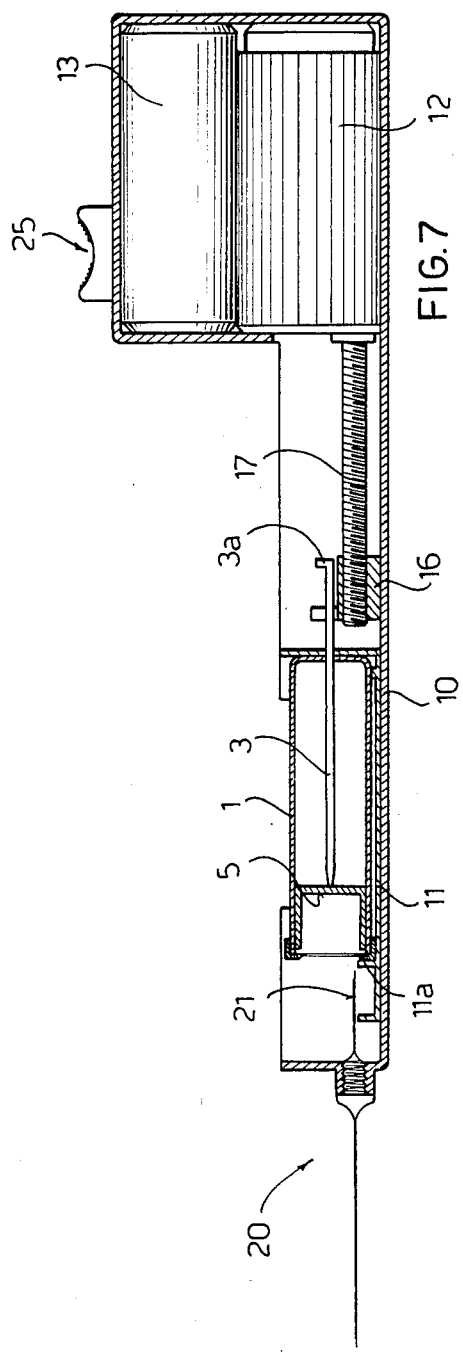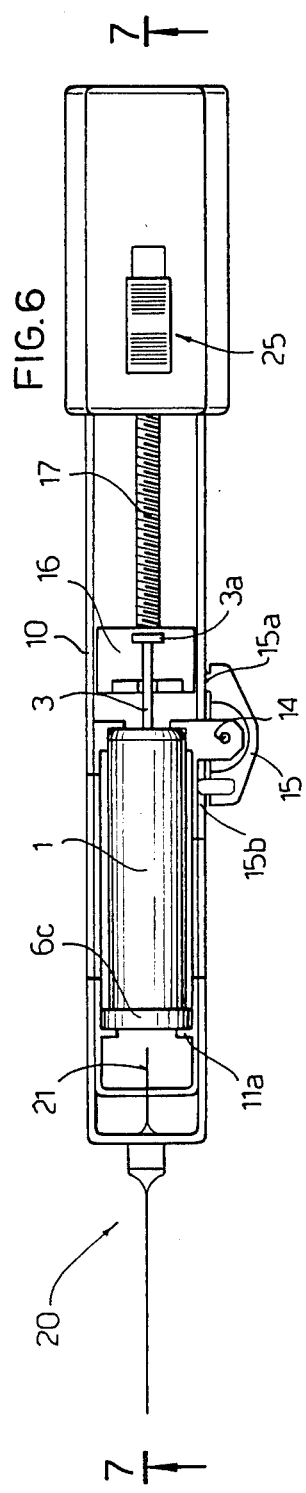

DEVICE FOR TAKING FROM A VEIN SAMPLES OF BLOOD TO BE TESTED

The present invention concerns a device for collection of blood specimens by venipuncture for laboratory testing.

There are numerous known devices for intravenous collection of blood specimens, such as re-usable glass syringes, disposable plastic syringes and vacuum collection systems. All there systems have many drawbacks, as far as concerns the safety of patient and analyst, as well as the quality of the specimen.

A brief description follows of the main drawbacks that occur with each of these systems.

If re-usable syringes are employed, cross-infection between patients is possible, whereas use of disposable syringes removes only the danger to patients and not the hazards for personnel carrying out the laboratory tests. It is during distribution into various containers of the blood held in the syringe that the analyst is exposed to the greatest risk, if the blood for testing is infected.

The vacuum system uses a double-ended needle, one end of which is inserted into the vein, while the other end is attached to one or more vacuum tubes which may already contain an anticoagulant. This system makes it possible to obtain a specimen that does not come into contact with the environment, at least not until it is opened in the laboratory, however, it has several other disadvantages.

The first is that the vacuum created in the tube during manufacture decreases with time because of inevitable leakages through the rubber tube stopper. If, on the other hand, the tube is of recent manufacture and therefore has a high vacuum, it breaks the more delicate blood cell membranes during the first stage of aspiration. Moreover, the glass inner surface releases ions into the drawn liquid and this restricts use of the vacuum system to certain types of test only, whereas use of inert plastic materials for vacuum systems must be ruled out because these materials are air-permeable.

The specimen in the vacuum tube is still in a partial vacuum after it has been drawn. This vacuum is nevertheless strong enough to cause a rebound when the tube is opened in the laboratory due to the sudden intake of atmospheric air, which expells the liquid from the tube with harmful consequences for the analyst.

There are also some practical aspects of the vacuum device for specimen collection that make sampling awkward for both patient and personnel. Vacuum systems in fact have a central needle which causes mechanical damage to the vein as needle entry tends to be perpendicular to the axis of the vein and not oblique, as is possible on the other hand, with an eccentric needle. Moreover, the syringes have a particularly thick rubber stopper to reduce vacuum loss to a minimum, but this stopper is difficult to puncture, so that sampling is more painful for the patient than with a conventional syringe.

The main purpose of the present invention is to eliminate or reduce to a minimum the drawbacks caused by the above systems, namely to obtain, with a single venipuncture using a double-ended needle, individual samplings forming a whole series of sealed specimens that will not contaminate the patient or the analyst, each one ready for the relevant test to be performed in the laboratory where it is sent in the sealed container itself.

Another purpose is to eliminate any transfer, making it possible to use the collection container as a normal test-tube that can be centrifuged.

Another purpose is to identify the specimens, i.e. to unequivocally match each specimen to the patient from whom it was taken, as well as to the test that is to be performed.

The main purpose has been achieved by creating a device for blood specimen collection consisting of an elongated support having at one end a double-ended needle consisting of an active needle that is inserted into the vein and a passive needle pointing towards the inside of the support. A disposable vial can be fitted into the cavity of the support preferably accessible from its outer jacket, and held there. This vial contains a plunger and preferably also a specific chemical reagent for the test that is to be performed; one end of the vial consists of a pierceable membrane, while the other end has an opening to accommodate the plunger operating means. Said means is preferably a flexible shaft, for example a band which has a pre-established breaking area at the point where it joins the plunger. The fact that the shaft is flexible ensures one-way movement of the plunger.

The shaft may have evenly spaced ridges on one of its surfaces or at least on one side of the band, said ridges being envisaged to come into contact with a flexible engaging means integral with the support or else with the disposable vial, in order to allow only an outward movement of the shaft, preventing any movement of the plunger towards the inside of the sleeve. An inward movement would in fact cause backflow into the vein of blood mixed with the chemical reagents contained in the vial, causing serious harm to the patient since said reagents are highly toxic.

The pierceable membrane of the vial may consist of a very thin, circular central portion to aid puncture by the needles attached to laboratory apparatus, and a thinned circular area around the central portion, to aid puncture by the passive needle integral with the support and pointing toward the inside of the support; the outer edge also has a portion serving to fix it to the vials.

The vial is preferably not placed directly in the cavity of the support, but is fitted into a cradle that slides within said support.

The vial contained in the sliding cradle can therefore move inside the support, thus occupying two extreme positions, one of which is defined by a catch that locks the vial in the sampling position. The first position occurs when the vial is inserted into the cradle; in this position the projecting end of the catch is disengaged. The second position is the operating or sampling position; this is achieved when the cradle in which the vial is held is pushed towards the passive needle which punctures the sleeve membrane, while at the same time the projecting end of the catch enters a corresponding opening in the support and the cradle respectively locking them together. At this point the shaft is brought into contact with the flexible engaging means. If the flexible engaging means in integral with the disposable vial, it is already set to engage with the shaft and the operator does not have to adjust it in any way. In this way the vial is fixed inside its cradle, which in turn is blocked and the device is ready for use.

Moreover, each vial is coded so that it can be unequivocally matched to the patient from whom the specimen was taken.

In a preferred embodiment the support has a mechanical system acting on a drive member connected to a gripping means that engages the shaft head and, by pulling the shaft, causes the plunger to slide. In this case it is not strictly necessary for the support or the vial to be equipped with the flexible shaft engagement means, the one-way outward movement of the shaft being ensured in any case by the drive member connected to the mechanical system.

The present invention will now be explained more fully on the basis of some examples of preferred embodiments illustrated in the attached drawings in which:

FIG. 1 is a sectional view of the vial alone without the support;

FIG. 2 is a plan view of the vial fitted into the support;

FIG. 3 is a view of a section along the line 3—3 of FIG. 2;

FIG. 4 is a plan view of an enlarged detail of the vial, namely of the membrane;

FIG. 5 is a view along section 5—5 of FIG. 4;

FIG. 6 is a plan view of the vial fitted into the support, according to a further improvement;

FIG. 7 is a view of the section along line 7—7 of FIG. 6.

FIG. 1 shows the vial 1 within which can slide the hollow plunger 5 joined by means of a pre-break area 4 to a shaft 3, in the form of a band with evenly spaced ridges on at least one side of the band. The closed end of the vial has a central opening 7 in which the shaft 3 slides; the other end is sealed by the pierceable membrane 6.

FIGS. 4 and 5 refer to the membrane 6 and show its special shape which enables it to be punctured by the passive needle in the circular area 6b and by the laboratory apparatus needle in the central portion 6a.

FIGS. 2 and 3 show the device with the vial 1 fitted into the sliding cradle 11 inserted in the support 10, but not yet positioned for use. It can be noted that the front part of the sliding cradle 11 is shaped so as to retain the vial and at the same time leave a free passage for the passive needle, having an open ledge 11a. The rear portion of said sliding cradle has a pin 14 on its side around which is mounted the revolving catch 15 equipped with a tooth 15a. By moving the catch 15 the tooth 15a is made to slide along a section of the outer surface of the support until it enters the opening 15b and sliding cradle 11 holding the vial is thus locked into place. In this way the counter-needle or passive needle 21 has punctured the membrane 6 in area 6b (FIGS. 4 and 5) and the shaft 3 is brought into contact with the flexible engaging means 23, said means 23 in this embodiment being integral with the support 10.

By pulling the end 3a of the shaft 3, the hollow plunger attached to the shaft is drawn and a vacuum is created inside the vial, so that the blood can flow into the vial until the hollow plunger 5 has reached the end of the vial with its closed end and the shaft 3 is pulled out completely. During this movement the shaft brings its ridges into contact with the flexible engaging means 23 which, when the shaft is pulled out, passes over the ridges in one direction only, allowing only the outward movement.

The operator again uses the catch 15 to unlock the sliding cradle and removes the vial 1; he then snaps off the shaft 3 at the predetermined breaking point 4, thus transforming the vial into a sealed test tube ready for laboratory tests. At this point a new vial 1 can be fitted into the cradle 11. Then all the operations described above may be repeated. The operating means 3 may be flexible so that it can only pull out the plunger, thus reliably preventing the reagent from entering the patient's vein.

In the embodiment shown in FIGS. 6 and 7, the plunger 3 is drawn by engaging the head 3a of the shaft with a gripping means 16 borne by a drive member 17 connected to a drive mechanism 12 that is fed by a battery 13. The mechanical system is operated by means of switch 25.

What I claim is:

1. A device for collecting a series of blood specimens for laboratory testing by a single venipuncture, comprising a support, means on the support for carrying a double pointed needle, and an elongated cradle mounted for lengthwise sliding movement on the support toward and away from the needle in the lengthwise direction of the needle, the cradle being open on one side to receive therein only by sideways insertion a disposable vial containing a plunger connected to an operating means for sliding the plunger in the vial toward and away from a pierceable membrane closing an end of the vial adjacent the needle, and the cradle being open at opposite ends thereof to receive at one end thereof said operating means and at the other end the needle.

2. A device according to claim 1, in combination with a said disposable vial having a said plunger therein having said operating means, said operating means being secured to the plunger at a predetermined breaking area to facilitate breaking off said operating means from said plunger when said plunger is withdrawn in the disposable vial as far as possible away from the needle.

3. A device according to claim 1, and drive means on said support adapted automatically to slide a said plunger inside a said vial in a direction away from the needle.

4. A device according to claim 1, in combination with a said disposable vial, said vial being elongated and cylindrical and having its axis parallel to but spaced from the axis of the needle whereby the needle enters a portion of said pierceable membrane spaced from the center of the pierceable membrane.

5. A device according to claim 1, and catch means engaging said cradle relative to the support thereby releasably retaining the support in a position advanced toward the needle and in which position the needle penetrates said membrane of said disposable vial within the cradle.

* * * * *